United States Patent [19]

Nakanishi

[11] Patent Number: 5,074,788

[45] Date of Patent: Dec. 24, 1991

[54] DEVICE FOR PREVENTING INTRUSION OF FOREIGN MATTER INTO DENTAL HANDPIECE

[75] Inventor: Takasuke Nakanishi, Kanuma, Japan

[73] Assignee: Nakanishi Dental Mfg. Co., Ltd., Tochigi, Japan

[21] Appl. No.: 661,398

[22] Filed: Feb. 26, 1991

[30] Foreign Application Priority Data

| Feb. 20, 1990 [JP] | Japan | 2-98062[U] |
| Aug. 24, 1990 [JP] | Japan | 2-87889[U] |
| Oct. 24, 1990 [JP] | Japan | 2-110519[U] |

[51] Int. Cl.$^5$ ............................. A61C 1/05; A61C 1/14
[52] U.S. Cl. ............................. 433/115; 433/129
[58] Field of Search ............... 433/115, 116, 122, 126, 433/127, 128, 129

[56] References Cited

U.S. PATENT DOCUMENTS

| 2,983,519 | 5/1961 | Staunt | 433/127 |
| 4,202,102 | 5/1980 | Nakanishi | 433/127 |
| 4,369,034 | 1/1983 | Garnier et al. | 433/115 |
| 4,975,056 | 12/1990 | Eibofner | 433/84 |

Primary Examiner—John J. Wilson
Assistant Examiner—Cindy A. Cherichetti
Attorney, Agent, or Firm—Charles E. Baxley

[57] ABSTRACT

A device for preventing intrusion of foreign matter into a dental handpiece includes an end cap secured to a bur sleeve for rotation in unison with the bur sleeve. Around the end cap, there are delimited gap sections the one end of which communicates with a forward or lower ball bearing positioned towards a tool inserting opening and the other end of which is opened at the foremost part of the handpiece. A discharge port passing through the main body of the handpiece and communicating with the gap sections is formed at the foremost part of the handpiece. With rotation of the bur sleeve, the end cap is rotated so that the pressure within the gap sections is decreased to suck the foreign matter, such as cut tooth particles or chips, which is expelled to outside through the discharge port under the centrifugal force of the end cap.

6 Claims, 5 Drawing Sheets

DEVICE FOR PREVENTING INTRUSION OF FOREIGN MATTER INTO DENTAL HANDPIECE

BACKGROUND OF THE INVENTION

This invention relates to a dental handpiece and, more particularly, to a device for preventing intrusion of foreign matter, such as cut tooth particles or chips to a bearing section within the dental handpiece.

A straight type of the currently used dental handpiece is shown as an example in FIG.5.

A main body of a dental handpiece C is constituted by a sheath section 10, a gripper section 11 and a nose section 12 provided at the middle, at the rear part and at the foremost part of a shell, respectively. Within the inside of the main body of the dental handpiece C, a spindle 2 connected to a driving motor, not shown, by means of a coupling 1, is rotatably supported for rotation by a forward side bearing 3 and a rear side bearing 4. A cylindrical pin-thrusting pipe 6 having a tapered forward end face 6a is slidably disposed on the outer periphery of the spindle 2 and is perpetually biased by a chuck spring 5 in a direction towards the foremost part of the handpiece C. Under the force of the chuck spring 5, the tapered face 6a abuts on a projection 7a of each of a plurality of bur-thrusting pins 7 for radially thrusting the bur-thrusting pins 7. A dental tool 9, introduced at a tool inserting opening 8, is clamped under the thrusting force exerted by the bur-thrusting pins 7 arranged on its periphery so as to be received and secured within the spindle 2.

With the above described dental handpiece C, the rotating spindle 2 is supported by bearings 3, 4 secured to the main body, so that there is necessarily provided a clearance to permit rotation of the spindle 2 between the main body and the rotating spindle 2.

On the other hand, it is known that, when the spindle 2 is rotated within the inside of the handpiece C, the air therein is stirred to induce a flow of air to lower the air pressure within the inside of the handpiece C as compared to the outside air pressure. The result is that a foreign matter, such as fine cut particles or chips of tooth, tends to be sucked into the inside of the handpiece C by way of a gap at the foremost part of the handpiece C between the tool inserting opening 8 and the dental tool 9. Such foreign matter may ultimately be charged in an inner gap 13 delimited between the nose section 12, the dental tool 9 and the foremost part of the spindle 2 to cause balls or a retainer of the forward side bearing 3 to wear or injure the ball race thereof.

SUMMARY OF THE INVENTION

It is a principal object of the present invention to provide a device for preventing intrusion of foreign matter, such as fine cut particles or chips of tooth into the inside of a dental handpiece, whereby such foreign matter occasionally introduced under suction into the inside of the handpiece may be prevented from injuring the bearing.

It is another object of the present invention to provide a device for preventing intrusion of foreign matter into the inside of the dental handpiece whereby the foreign matter may be spontaneously expelled to the outside of the main body of the handpiece.

The above and other objects of the present invention will become more apparent from the following description.

In accordance with the present invention, there is provided a device for preventing intrusion of foreign matter into a dental handpiece comprising a rotatable bur sleeve for rotatably receiving and securing a dental tool introduced through a tool inserting opening and a bearing for rotatably supporting the bur sleeve with respect to a stationary main body of the handpiece. The device for preventing intrusion of foreign matter into the handpiece comprises a rotatable member secured to the bur sleeve for rotation in unison with the bur sleeve, a gap section formed on the outer periphery of the rotatable member for communicating at one end thereof with the bearing and opening at the other end thereof at the distal end of the handpiece, and a discharge port formed in the vicinity of the distal end of the dental handpiece, the discharge port passing through the join body of the handpiece and communicating with the gap section, whereby the foreign matter including cut tooth particles is sucked into the gap section so as to be expelled to outside of the main body of the handpiece through the discharge port under the centrifugal force induced by rotation of the rotatable member.

PREFERRED EMBODIMENTS OF THE INVENTION

Figure 5:
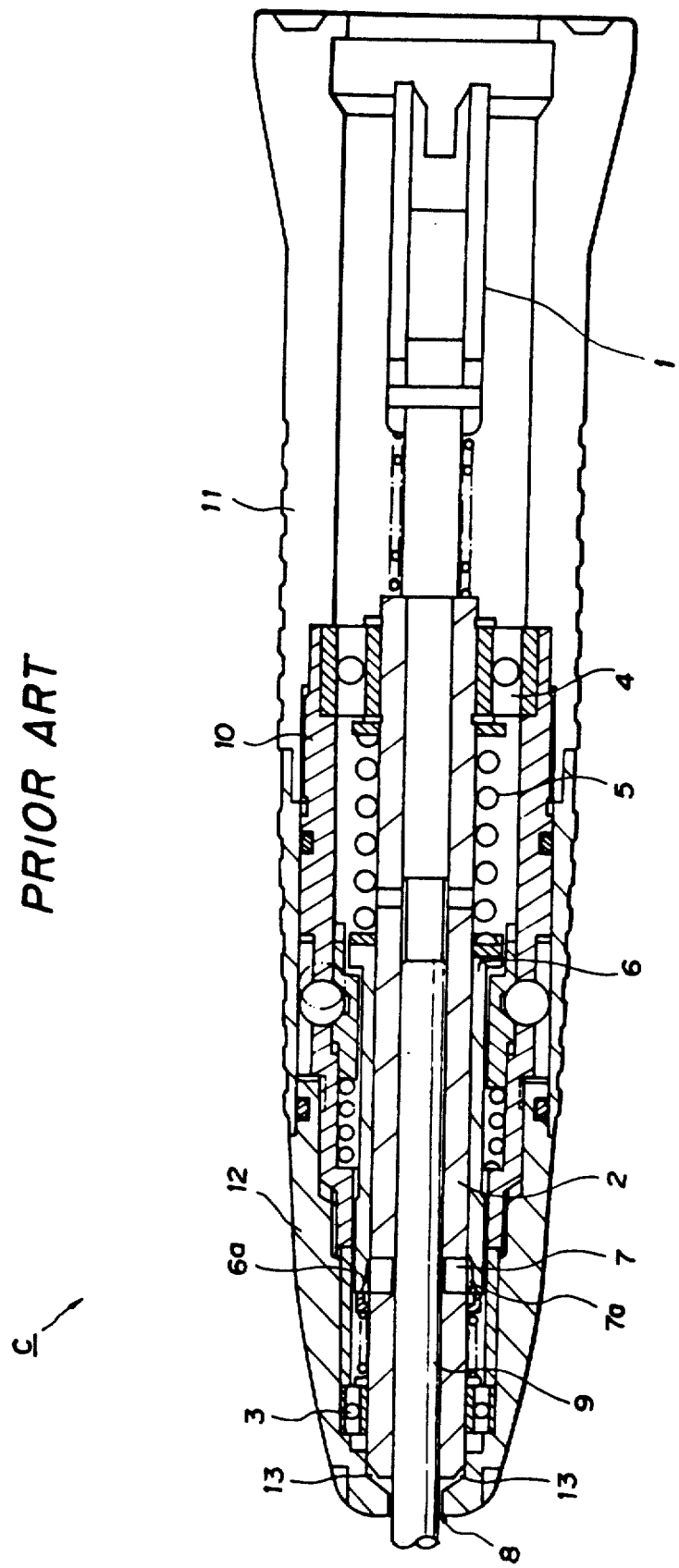
FIG.5 is an enlarged longitudinal cross-sectional view showing the foremost part of a conventional dental handpiece.

By referring to the drawings, certain preferred embodiments of the present invention will be explained in detail. It is noted that parts or components similar in operation to those of the dental handpiece already described in connection with FIG.5 are indicated by the same reference numerals and the corresponding description is omitted for simplicity.

Figure 1:
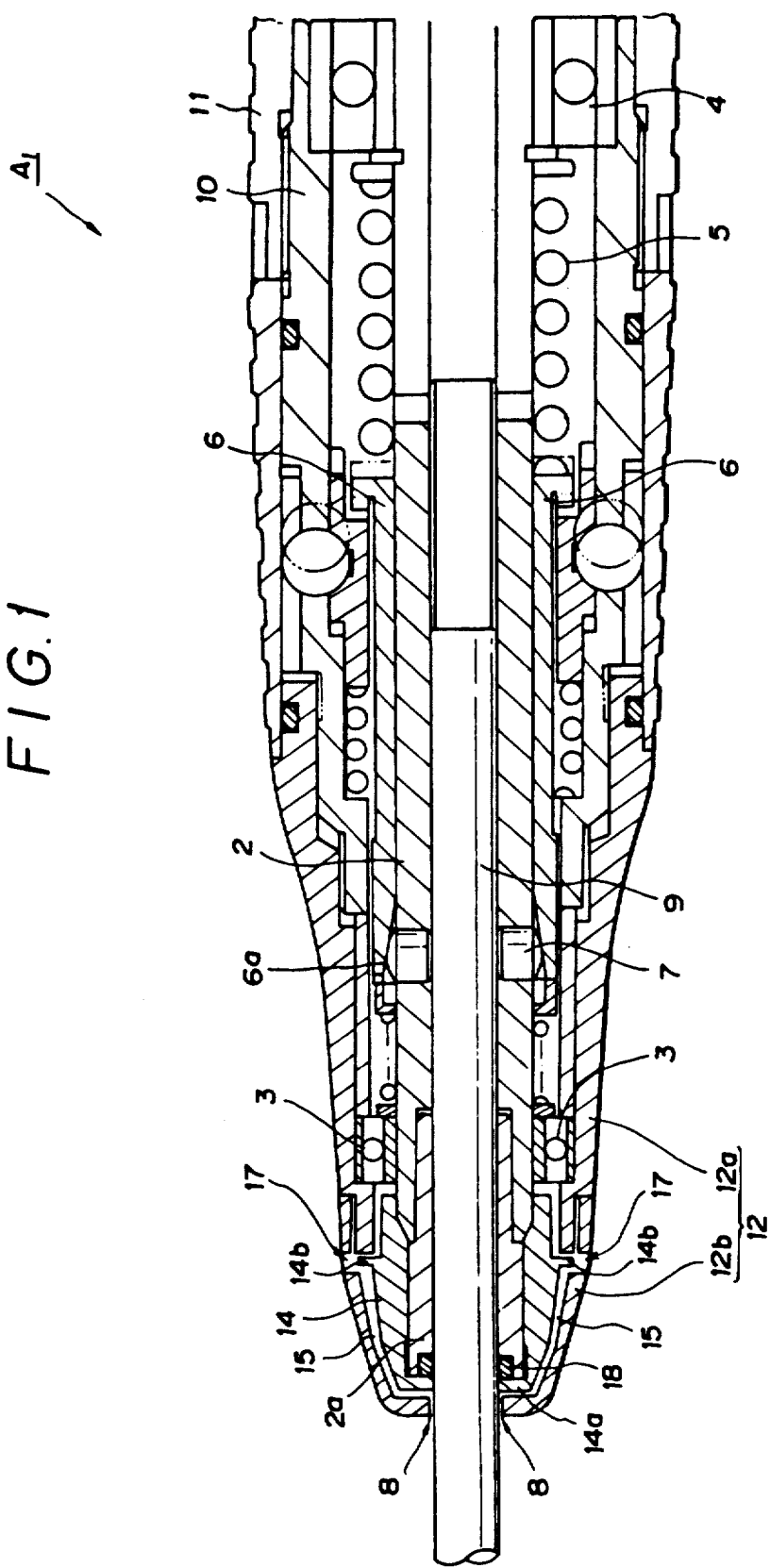
FIG.1 is an enlarged longitudinal cross-sectional view showing the foremost part of a straight type handpiece equipped with a device for preventing intrusion of foreign matter into the handpiece according to an embodiment of the present invention.

FIG.1 shows a straight type dental handpiece A1, the main body of which is constituted by a sheath section 10, gripper section 11 and a nose section 12 at the middle, at the rear end and at the foremost part of a shell, respectively. The nose section 12 is made up of a main nose member 12a and a nose cap 12b detachably mounted, such as by threading, on the one end of the main nose member 12a.

The nose cap 12b is provided with four equiangularly spaced radial discharge ports 17. A spindle joint 2a constituting a bur sleeve adapted for receiving and securing a dental tool 9 in cooperation with a spindle 2 is mounted radially inwardly of the foremost part of the spindle 2. An end cap 14 as an additional rotating member is threadedly mounted on the outer end periphey of the spindle joint 2a.

The end cap 14 has an inner flange section 14a contacting at the radially inner end thereof with the dental tool 9 and a radially outwardly projecting outer flange section 14b, and is intimately contacted with the outer peripheries of the spindle 2 and the spindle joint 2a. A gap section 15 communicating at one end with a tool inserting opening 8 and at the other end with a forward side ball bearing 3 is delimited between the outer periphery of the end cap 14 and the nose cap 12b.

The operation of the intrusion preventing device for the dental handpiece A1 is hereinafter explained.

When the spindle 2 is rotated upon cutting a tooth, the spindle joint 2a and the end cap 14 are rotated in unison and, as a result of rotation of these components, a flow of air is induced around these components. Since the radius of rotation of the end cap 14 is larger than that of the spindle 2 or that of the spindle joint 2a, the circumferential velocity of the end cap 14 is higher than that of the spindle 2 or that of the spindle joint 2a. Above all, the radius of rotation of the outer flange section 14b is the largest and hence the air flow velocity around the outer periphery of the outer flange section 14b is the highest so that the air pressure around the outer flange section 14b is lowest in the vicinity of the foremost part of the handpiece A1.

In effect during cutting of for example, a tooth, a foreign matter such as fine cut particles or chips are introduced at the gap of the tool inserting opening 8 under suction due to a pressure decrease induced within the handpiece A1. This foreign matter is introduced into the annular gap section 15 where the air pressure is lower to reach the area of the outer flange section 14b where the pressure is the smallest. The foreign matter is then expelled to outside through the discharge ports 17 under the centrifugal force of the end cap 14. In this manner, the foreign matter can be prevented from being intruded to the area of the forward side ball bearing 3.

Figure 2:
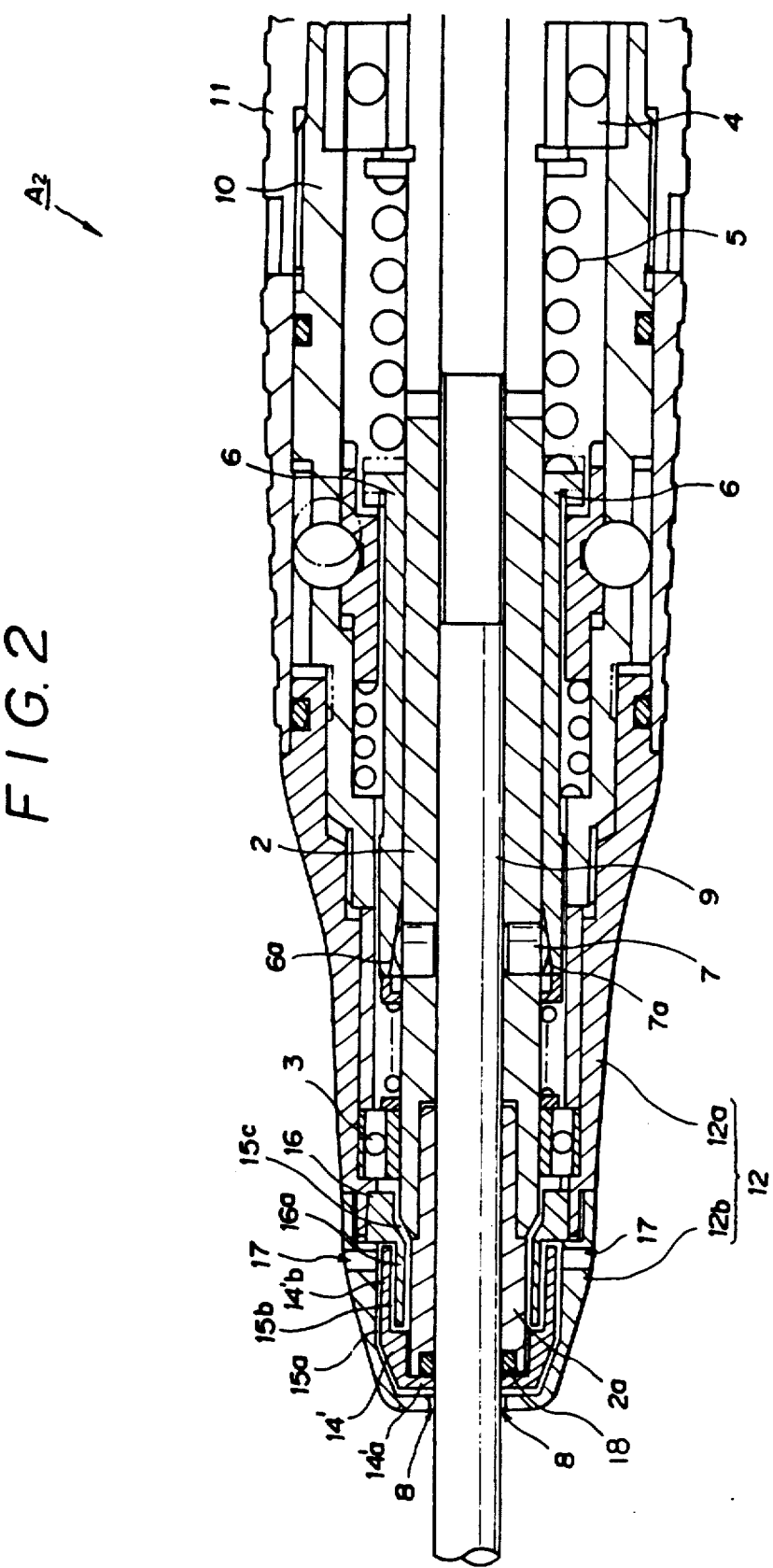
FIG.2 is a cross-sectional view similar to FIG.1 and showing a straight type handpiece equipped with the device for preventing intrusion of foreign matter into the handpiece according to a modified embodiment of the present invention.

FIG.2 illustrates a dental handpiece A2 equipped with a modified embodiment of the intrusion preventing device according to the present invention.

An end cap 14' has an inner flange section 14'a, having an end section abutting on the dental tool 9, and a cylindrical partition 14'b extending towards the rear side of the handpiece A2. An annular gap section 15a communicating with the tool inserting opening 8 is delimited between the nose cap 12b and the partition 14'b.

On the inner periphery of the distal end of the main nose member 12a, there is provided a collar 16, as a fixed stationary partitioning member, having a cylindrical partition 16a extending towards the distal end of the handpiece A2. A second gap section 15b communicating with the gap section 15a is delimited between the partition 16a and the partition 14'b of the end cap 14'. The collar 16 has its proximal end secured to the main nose member 12a, so that, during rotation of the spindle 2, the collar 16 remains stationary. A third gap section 15c communicating with the area of the forward side bearing 3 and the second gap section 15b is defined between the inner periphery of the collar 16, and the outer peripheries of the spindle 2 and the spindle joint 2a. Thus, the gap sections 15a, 15b and 15c are kept in communication with one another from the tool inserting opening 8 through to the forward side bearing 3.

The operation of the intrusion preventing device for the dental handpiece A2 is hereinafter explained.

When the spindle 2 is rotated upon cutting, for example, a tooth, the spindle joint 2a and the end cap 14' are rotated in unison therewith and the air pressure within the handpiece A2 is lowered with rotation of these components. Since the radius of rotation of the end cap 14' is larger than that of the spindle 2 or that of the spindle joint 2a, the circumferential velocity of the end cap 14' is higher than that of the spindle 2 or that of the spindle joint 2a. Since the partition 16a of the collar 16 is positioned between the end cap 14' on one hand and the spindle 2 and the spindle joint 2a on the other, the aforementioned gap sections 15c and 15b where the air flows with different circumferential velocities are defined radially inwardly and outwardly of the partition 16a, respectively.

On the other hand, the circumferential velocity through the gap section 15a defined on the outer periphery of the end cap 14' is higher than that through the gap section 15b defined on the inner periphery of the end cap 14' on account of the difference in the radius of rotation. Thus, the circumferential velocities through the gap sections 15c, 15b and 15a are higher in this order and hence the air pressures prevailing in these gap sections 15c, 15b and 15a are lower in the same order. In this manner, the air pressure in the gap section 15a is the smallest in the vicinity of the foremost part of the handpiece A2.

In effect, during cutting of, for example, a tooth, a foreign matter such as fine cut particles or chips are introduced at the gap of the tool inserting opening 8 under suction due to pressure decrease within the handpiece A2. This foreign matter is introduced into the gap section 15a where the air pressure is lower. However, it is hardly introduced into the gap sections 15b, 15c where the air pressure is higher than that in the gap section 15a. Thus, the foreign matter can hardly be introduced into the gap section 15c lying closely to the forward side ball bearing 3, thus reducing the damages to the bearing 3 caused by the foreign matter, such as fine cut tooth particles or chips.

In this manner, the foreign matter is expelled to outside under the centrifugal force through the discharge ports 17 around the end cap 14'. Since the foreign matter may be left in the gap sections, it is preferred to dismantle the nose cap 12b and the end cap 14' to take out the residual foreign matter periodically. An O-ring 18 is provided between the inner flange section 14'a and the spindle joint 2a for preventing the foreign matter from being intruded into the inside of the spindle 2 by the dental tool 9 during the exchanging operation of the dental tool 9.

Figure 3:
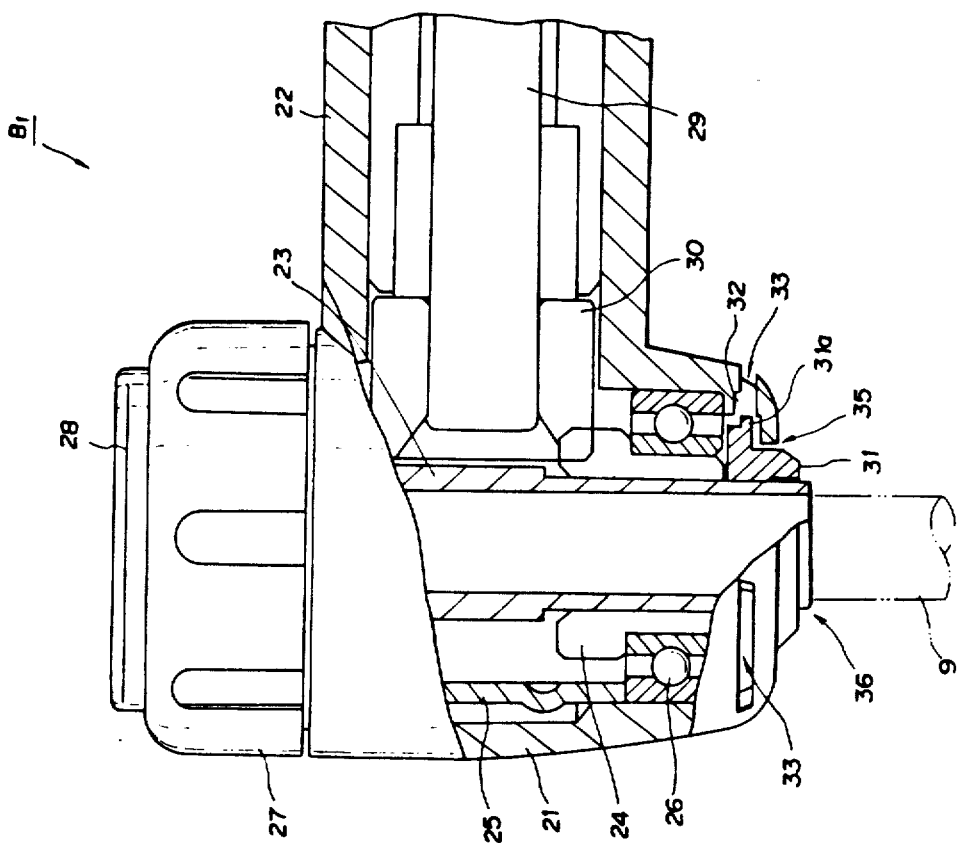
FIG.3 is an enlarged longitudinal cross-sectional view showing the foremost part of an angle type handpiece equipped with the device for preventing intrusion of foreign matter into the handpiece shown in FIG.1.

FIG.3 illustrates another modified embodiment of the intrusion preventing device of the present invention, when applied to an angle type dental handpiece B1.

The main members of the foremost part of the dental handpiece B1 include a head housing 21 adapted for attaching a dental tool 9, and a head housing jacket 22. Within the head housing 21, as the main body of the handpiece B1, there are provided a bur sleeve 23 for receiving and securing the dental tool 9 introduced through a tool inserting opening 36, a head gear 24 for roatationally driving the bur sleeve 23, and an upper ball bearing, not shown, and a lower ball bearing 26, arranged between both ends of a bearing spacer 25.

On the upper part of the head housing 21 is threadedly mounted a head cap 27 in the inside of which there is provided a chucking device, not shown, wherein the dental tool 9 may be detachably retained by manually thrusting or releasing a pushbutton 28. A driving shaft 29, rotated by a driving electric motor, not shown, is mounted in the head housing jacket 22, and a driving gear 30 for meshing with the head gear 24 for transmitting rotation of the driving shaft 29 to the bur sleeve 23 is mounted on the distal end of the driving shaft 29.

On the lower outer periphery of the bur sleeve 23, there is mounted an end cap 31, as a rotating member, formed with a radially outwardly extending outer flange section 31a and having its one end threadedly secured to the bur sleeve 23. The end cap 31 may be rotated in this manner in unison with the bur sleeve 23. Between the outer flange section 31a and the head housing 21 corresponding to the outer periphery of the flange section 31a, there is defined a gap section 32 communicating at one end with a downwardly opening port 35 and at the other end with the area of the lower ball bearing 26. The lower end of the head housing 21 is formed with a plurality of radial slits 33 as discharge ports communicating with the gap section 32.

The operation of the intrusion preventing device for the angle type dental handpiece B1 is hereinafter explained.

When the bur sleeve 23 is rotated upon cutting, for example, a tooth, the end cap 31 is rotated in unison therewith and the air pressure in the inside of the handpiece is lowered due to rotation of these components. The radius of rotation of the outer flange section 31a of the end cap 31 is the largest, as long as the foremost part of the handpiece B1 and the near-by area are concerned, at the gap section 32 communicating from the port 35 to the lower ball bearing 26, so that the area around the gap section 32 is rotated with the maximum circumferential velocity with rotation of the bur sleeve 23. Hence, as long as the foremost part of the handpiece B1 is concerned, the air pressure in the gap section 32 around the outer flange section 31a is the smallest.

In effect, during cutting, for example, a tooth, a foreign matter such as fine cut particles or chips are introduced through the port 35 under suction due to pressure decrease within the handpiece B1. This foreign matter is introduced into the gap section 32 and thence into the area of the outer flange section 31a where the pressure is the smallest. The foreign matter is then expelled to outside through the slits 33 under the centrifugal force of the end cap 31.

Figure 4:
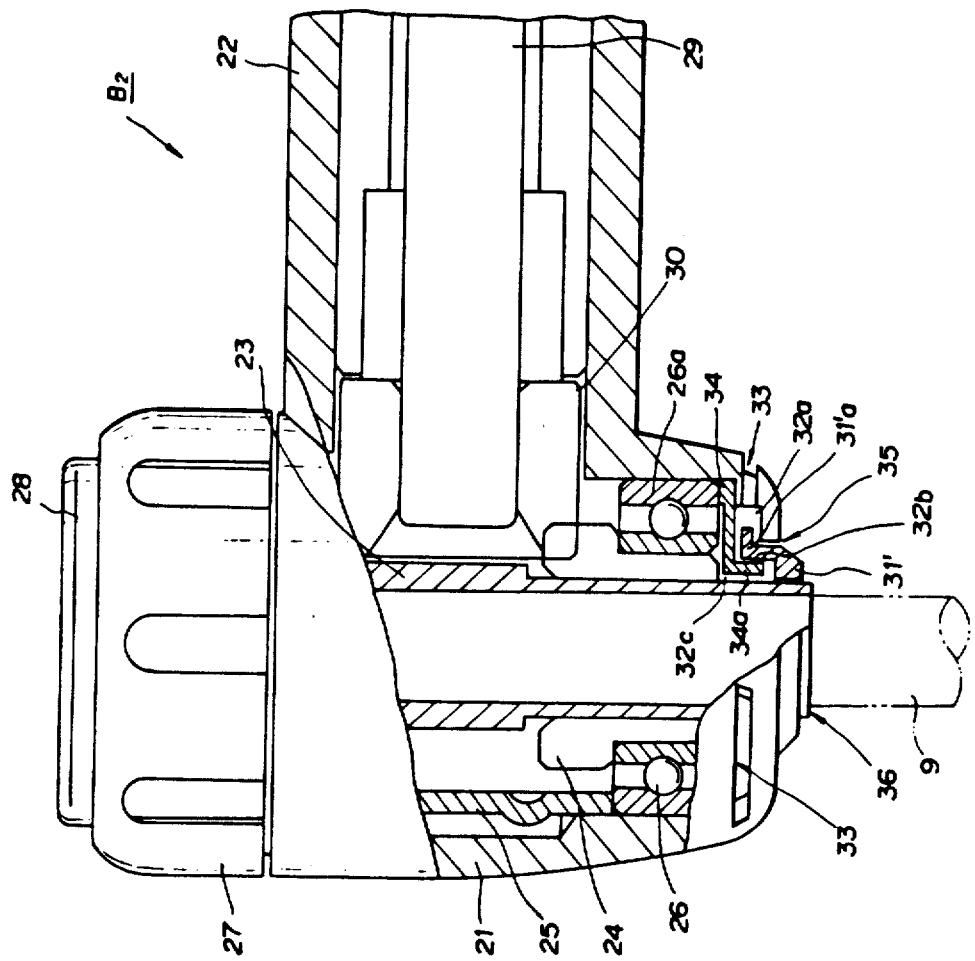
FIG.4 is an enlarged longitudinal cross-sectional view similar to FIG.3 and showing an angle type dental handpiece equipped with the device for preventing intrusion of foreign matter into the handpiece shown in FIG.2.

FIG. 4 illustrates another modified embodiment of an intrusion preventing device for a dental handpiece B2 according to the present invention.

On the lower outer periphery of the bur sleeve 23, there is mounted an end cap 31', as a rotatable partitioning member, which is provided with an annular outer flange section 31'a having an L-shaped cross-section and which has its one end threadedly secured to the bur sleeve 23. Thus, the end cap 31' is rotated in unison with the bur sleeve 23. Between the outer flange section 31'a and the head housing 21 corresponding to the outer periphery of the outer flange section 31'a, there is delimited a gap section 32a communicating with the port 35 which is opened downwards. In a lower portion of the head housing 21, there are formed a plurality of radial slits 33 communicating with the gap section 32a.

On the lower inner periphery of the head housing 21, an outer race 26a of the lower ball bearing 26 and a collar 34 as a stationary partitioning members are placed. The collar 34 is pressed and secured against a radially inwardly extending lip of the head housing 21 under the downward thrusting pressure exerted by the bearing spacer 25. This downwardly directed thrusting pressure of the bearing spacer 25 is produced by threading the head cap 27 downwards and transmitted to the bearing spacer 25 by means of an outer race of the upper ball bearing, not shown. Since the collar 34 is pressed between the outer race 26a and the lower inner periphery of the head housing 21 so as to be secured unitarily to the head housing 21, the collar 32 remains stationary even when the bur sleeve 23 is rotated.

A cylindrical partition 34a of the collar 34 is provided for extending along the longitudinal axis of the bur sleeve 23 and a second gap section 32b communicating with the gap section 32a is delimited between the outer periphery of the partition 34a and the inner periphery of the outer flange section 31'a. Between the inner periphery of the partition 34a and the bur sleeve 23, there is defined a third gap section 32c communicating at one end with the lower ball bearing 26 and at the other end with the second gap section 32b. Thus, the gap sections 32a, 32b and 32c are in communication with one another from the port 35 through to the lower ball bearing 26.

The operation of the above described intrusion preventing device for the angle type dental handpiece B2 is hereinafter explained.

When the bur sleeve 23 is rotated upon cutting, for example, a tooth, the end cap 31' is rotated in unison therewith and the air pressure within the inside of the handpiece B2 is lowered as a result of rotation of these components. As long as the gap extending from the port 35 to the lower ball bearing 26 is concerned, the outer flange section 31'a of the end cap 31' has the largest radius of rotation and hence exhibits the largest circumferential velocity during rotation of the bur sleeve 23. Since the partition 34a of the collar 34 is positioned between the bur sleeve 23 and the outer flange section 31'a, the air flow velocities are different on the radially inner and radially outer sides of the partition 34a. On the other hand, since the radius of rotation of the inner periphery of the outer flange section 31'a of the end cap 31' is different from that of the outer periphery thereof, the circumferential velocity of the outer periphery with the larger radius of rotation is higher than that of the inner periphery. Thus, the air flow velocities through the gap sections 32c, 32b and 32a are higher in this order and the air pressures therein are lower in the same order. In this manner, as long as the distal end of the handpiece B2 is concerned, the air pressure within the gap section 32a is the smallest.

When the tooth or the like is actually cut, a foreign matter such as cut particles or chips is introduced thought the port 35 under suction induced by the pressure decrease in the inside of the handpiece B2. While this foreign matter is introduced into the gap section 32a with the smallest pressure, it is hardly introduced into the gap sections 32b or 32c where the air pressure is higher than in the gap section 32a. The foreign matter thus sucked is discharged by the centrifugal force of the end cap 31' to outside through the slits 33 provided in the lower outer periphery of the head housing 21.

In the present embodiment, the collar 34 as the stationary partitioning member is secured to the lip on the lower inner end of the head housing 21 under the downward thrusting pressure exerted by the outer race 26a of the lower ball bearing 26. However, the collar 34 may be secured in the inside of the head housing 21 directly or indirectly in any other way, if the collar remains stationary and non-rotatable during rotation of the bur sleeve 23.

Although the present invention has been described with reference to the preferred embodiments, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. In a dental handpiece comprising in combination a rotatable ur sleeve for rotatably receiving and securing a dental tool introduced through a tool inserting opening and a bearing for rotatably supporting said bur sleeve with respect to a stationary main body of the handpiece, an improvement wherein said handpiece comprises in combination a device for preventing intrusion of foreign matter into inside of the handpiece, including:

a rotatable member secured to said bur sleeve for rotation inunison with said bur sleeve, a gap section formed on an outer periphery of said rotatable member for communicating at one end thereof with said bearing and opening at the other end thereof at a distal end of said handpiece, and a discharge port formed in the vicinity of the distal end of the entail handpiece, said discharge port passing through said man body of the handpiece and communicating with said gap section, wherein a stationary partitioning member secured to said main body of the handpiece is provided on an outer periphery of said bur sleeve for delimiting a first gap section communicating with said bearing, said gap section includes said first gap section, a second gap section delimited between an outer periphery of said stationary partitioning member and an inner periphery of said rotatable member, and communicating with said first gap section, and a third gap section formed on the outer periphery of said rotatable member, said third gap section communicating at one end thereof with said second gap section and opening in the vicinity of the distal end of the dental handpiece, wherein, with rotation of said bur sleeve, air pressure within said gap sections is decreased in sequence of said first gap section, said second gap section and said third gap section, and whereby the foreign matter including cut tooth particles is sucked into said gap sections so as to be expelled to outside on the main body of the handpiece through said discharge port under centrifugal force induced by rotation of said rotatable member.

2. The device according to claim 1, wherein aid rotatable member includes an outer flange section projecting radially outwardly in register with said discharge port.

3. The device according o claim 1, wherein said stationary partitioning member includes a rotatable cylindrical partition radially outwardly of said bur sleeve for delimiting said fist gap section.

4. The device according to claim 3 wherein said rotatable member includes a rotatable cylindrical partition or delimiting said second gap section radially outwardly of said stationary partitioning member and said third gap section radially outwardly of said rotatable cylindrical partition.

5. The device according to claim 1 wherein said stationary main body of the handpiece comprises non-rotatable members.

6. The device according to claim 5 wherein said non-rotatable members include a sheath section, a gripping section, a nose section and a head housing.

* * * * *